United States Patent
Schluesselberger, Sr. et al.

(10) Patent No.: US 10,456,919 B2
(45) Date of Patent: Oct. 29, 2019

(54) MANIPULATOR ARRANGEMENT AND MOVEMENT DEVICE

(71) Applicant: AMST-SYSTEMTECHNIK GMBH, Ranshofen (AT)

(72) Inventors: Richard Schluesselberger, Sr., Braunau am Inn (AT); Richard Schluesselberger, Jr., Braunau am Inn (AT); Rainer Schluesselberger, Braunau am Inn (AT); Norman Eisenkoeck, Grieskirchen (AT)

(73) Assignee: AMST-Systemtechnik GmbH, Ranshofen (AT)

( * ) Notice: Subject to any disclaimer, the term of this patent is extended or adjusted under 35 U.S.C. 154(b) by 1287 days.

(21) Appl. No.: 14/400,059

(22) PCT Filed: May 6, 2013

(86) PCT No.: PCT/EP2013/059342
§ 371 (c)(1),
(2) Date: Nov. 10, 2014

(87) PCT Pub. No.: WO2013/167511
PCT Pub. Date: Nov. 14, 2013

(65) Prior Publication Data
US 2015/0099970 A1    Apr. 9, 2015

(30) Foreign Application Priority Data

May 8, 2012    (AT) .................................. A 547/2012

(51) Int. Cl.
*B25J 11/00*    (2006.01)
*B25J 17/02*    (2006.01)
(Continued)

(52) U.S. Cl.
CPC ................. *B25J 11/00* (2013.01); *A61B 8/40* (2013.01); *B25J 9/16* (2013.01); *B25J 17/0208* (2013.01); *G09B 19/00* (2013.01); *Y10S 901/02* (2013.01)

(58) Field of Classification Search
CPC . G09B 9/006; G09B 9/12; G09B 9/30; G09B 19/00; A61B 8/40; B25J 9/16; B25J 17/0208; Y10S 901/02
See application file for complete search history.

(56) References Cited

U.S. PATENT DOCUMENTS 4,619,506 A    10/1986    Repperger et al.
4,890,629 A    1/1990    Isasi Capelo et al.
(Continued)

FOREIGN PATENT DOCUMENTS

DE    19637884 A1    4/1998
RU    2114772 C1    7/1998
RU    18138 U1    5/2001

OTHER PUBLICATIONS

Ryohei Takeuchi et al., "Field Testing of a Remote Controlled Robotic Tele-echo System in an Ambulance Using Broadband Mobile Communication Technology", J Med Sys (2008) 32: pp. 235-242, published online Jan. 29, 2008, DOI 10.1007/s10916-008-9128-x.

(Continued)

*Primary Examiner* — Carl H Layno
*Assistant Examiner* — Dacheng Xie
(74) *Attorney, Agent, or Firm* — Laurence A. Greenberg; Werner H. Stemer; Ralph E. Locher

(57) ABSTRACT

A movement device and a manipulator configuration are provided for contact and/or invasive examination or treatment of the human or animal body under the influence of increased and/or changing acceleration. Wherein a functional head can be moved relative to a base along a plurality (Continued)

of degrees of freedom movable by drive devices and at least one drive device is constituted as a force-limited drive device.

18 Claims, 7 Drawing Sheets

(51) Int. Cl.
*G09B 19/00* (2006.01)
*A61B 8/00* (2006.01)
*B25J 9/16* (2006.01)

(56) References Cited

U.S. PATENT DOCUMENTS

| | | | |
|---|---|---|---|
| 5,051,094 A * | 9/1991 | Richter | G09B 9/006 |
| | | | 434/30 |
| 2011/0126660 A1* | 6/2011 | Lauzier | B25J 17/0208 |
| | | | 74/490.05 |

OTHER PUBLICATIONS

Pal J. From et al., "Modeling and Motion Planning for Mechanism on a Non-Inertial Base", 2009 IEEE International conference on Robotics and Automation, Kobe International Conference Center, Kobe, Japan, May 12-17, 2009, pp. 3320-3326.

Ole Jakob Elle, "Sensor Control in Robotic Surgery" Dr.ing-thesis, Rikshospitalet, University of Oslo, NTNU, Department of Production and Quality Engineering, Faculty of Engineering Science and Technology, Norwegian Jniversity of Science and Technology, Oslo Aug. 2003—Part 1—140 pages.

Ole Jakob Elle, "Sensor Control in Robotic Surgery" Dr.ing-thesis, Rikshospitalet, University of Oslo, NTNU, Department of Production and Quality Engineering, Faculty of Engineering Science and Technology, Norwegian University of Science and Technology, Oslo Aug. 2003—Part 2—124 pages.

Jacheung Park, "Control Strategies for Robots in Contact", A Dissertation submitted to the Department of Aeronautics and the Committee on Graduate Studies of Stanford University in partial fulfillments of the requirements for the Degree of Doctor of Philosophy, Mar. 2006, 160 pages.

Wikipedia, "Strain Gauge", retrieved from: https://en.wikipedia.org/w/index.php?title=Strain_gauge&oldid=899192058. The page was last edited on May 28, 2019.

* cited by examiner

MANIPULATOR ARRANGEMENT AND MOVEMENT DEVICE

BACKGROUND OF THE INVENTION

Field of the Invention

The invention relates to a manipulator arrangement for the contact and/or invasive examination or treatment of the human or animal body under the influence of increased and/or changing acceleration and a movement device with at least one fixing device for accommodating and/or fixing a human or animal body, which is provided on a first carrier element which is disposed rotatably around a first main axis, as well as the use of a manipulator arrangement in a movement device.

For the training of pilots or for the preparation of persons for increased, changing acceleration states, devices are known wherein the fixing device for accommodating and/or fixing a person is disposed rotatably around a first main axis. The person experiences increased acceleration as a result of the rotation at a certain standard distance from the main rotational axis. The magnitude of the acceleration is made up of the radial acceleration and the gravitational acceleration. The magnitude of the vector can thus be varied by changing the angular velocity around the first main axis and/or by changing the standard distance.

Furthermore, further degrees of freedom and drive arrangements can be provided in order to position the human or animal body in the movement device relative to the resultant acceleration vector. The position of the resultant acceleration vector with respect to the body position of the person can thus be selected by this positioning.

Examples of such devices are flight simulators, one-arm centrifuges, multi-arm centrifuges with a traversable carriage, multi-arm centrifuges with a traversable heave carriage, medical centrifuges with a plurality of nacelles disposed rotatably around a main axis etc. EP2351001 A1, for example, shows a generic device.

For the monitoring of the bodily functions of the occupants of such movement devices, parameters such as pulse or respiration rate can be measured according to the prior art. However, further measurements such as for example ultrasound images of organs, blood analyses or suchlike are not possible in systems with increased or changing acceleration. The reason for this is that, due to the change in the acceleration, the organs of the body also experience a movement in the body and at least partially change position. Furthermore, parts of the body or the whole body are possibly also moved due to the influence of increased acceleration. In the case of measurement instruments fitted statically fixed on the body, it may therefore happen that the measurement results are falsified by the described changes in the body and do not therefore provide meaningful information. In order to improve the examination or the treatment, it is therefore necessary to provide for the possibility of adjustments to the measurement instrument. Since, however, a treatment or an examination by medical personnel, for example, is not possible in systems with increased or changing acceleration, the actions would have to be carried out by manipulation devices or robots. Furthermore, a remote-controlled operation for protection of the operating personnel is also advantageous when use is made of a radiation source on the functional head, e.g. for x-ray photographs.

Robots or manipulation devices corresponding to the prior art are however not suitable for withstanding the loads in, for example, a centrifuge or suchlike. Furthermore, robots or manipulator arrangements corresponding to the prior art comprise controls which are not equipped and designed to take account of increased or changing accelerations. Moreover, in examinations of test subjects by robots, there is an increased risk of injuries occurring in the event of malfunctions of the robot.

BRIEF SUMMARY OF THE INVENTION

The problem of the invention is to provide a movement device and a manipulator arrangement, which is suitable and equipped to enable an examination or treatment of a human or animal body with increased or changing acceleration. This includes the sub-problems consisting in the fact that the examination can be carried out remote-controlled, from a position outside the movement device, that the examination is carried out by a manipulator arrangement which is designed to be used in systems with changing or increased acceleration and that inadvertent injury to the body by the manipulator arrangement is eliminated.

The problem according to the invention is solved by the fact that a functional head can be moved relative to a base along a plurality of degrees of freedom movable by drive devices and that at least one drive device is constituted as a force-limited drive device.

For this purpose, provision can be made such that the contact force between the functional head and the body is limited systemically by the force-limited drive device, in particular that the contact force is limited by means of a pressure valve of the force-limited drive device, that the contact force can be selected and/or that the pressure valve is constituted as a control valve. Furthermore, the device according to the invention comprises the features that, when the selected maximum contact force is exceeded, the movement element of the force-limited drive device is essentially decoupled from the base element of the force-limited drive device. The decoupling takes place for example by the opening of the pressure relief valve.

Furthermore, the device according to the invention preferably comprises the features that the drive devices are controlled and/or regulated by one or more control systems and that the drive devices and the control systems are equipped for operation with increased and/or changing acceleration, that the position and/or the contact force of the functional head touching the body is variable with respect to the body under the influence of increased and/or changing acceleration and/or that the functional head can be guided towards the body in a selectable position.

Further features according to the invention can be that the force-limited drive device comprises one or more piston-less pneumatic actuators, one or more air muscle arrangements, one or more air bellows arrangements, one or more pneumatic cylinder arrangements with pneumatic cylinders with pistons mounted essentially free from adhesive friction, one or more gearless electric linear units with armatures mounted essentially free from adhesive friction and/or one or more guides, that the drive devices comprise a linear axis, a rack-and-pinion drive, a parallel kinematic drive, a hexapod, a tripod, a robot arm, a rotary drive, a cardan-shaft drive and/or a Cartesian drive and/or that the drive devices each comprise a base element, a movement element and a drive for moving the movement element with respect to the base element along the degree or respective degrees of freedom and/or that the drive devices are lined up in series, wherein the movement element of a drive device is in each case connected or coupled to the base element of the following drive device.

Furthermore, provision can be made such that the movement of the functional head with respect to the base can be remote-controlled and/or automated, in particular can be remote-controlled and/or automated by means of one or more control systems and/or one or more data input arrangements, that the data input arrangement comprises input devices such as joysticks, slider controls, data gloves, computer programs, automated programs and/or similar arrangements, that the functional head comprises components, examination and/or treatment devices such as for example an ultrasound measuring head, optical recording devices, acoustic recording devices, resistance measuring devices, an injection arrangement, a liquid analysis arrangement, a blood-taking device, an analysis device, a chemical analysis device, a radiation source, e.g. x-ray, gamma or infrared radiation, a laser source, sample-taking devices, temperature measuring devices, current measuring devices, radiation detection devices, endoscopic examination devices, devices for optical eye examination and/or further radiological, invasive or contact devices for diagnostic or therapeutic purposes.

Features of the invention may also be that a manipulator arrangement according to the invention is disposed on a movement device according to the invention, that the movement device is constituted as a flight simulator, as a one-arm centrifuge, as a centrifuge with a traversable carriage, as a centrifuge with a traversable heave carriage, as a training centrifuge, as a training centrifuge for use under zero gravity, as a medical centrifuge or as a medical centrifuge with a plurality of nacelles disposed rotatably around a first rotational axis, that a base carrier element coupled or connected to the first carrier element is provided, said base carrier element being connected, coupled or capable of being connected to the base of the manipulator arrangement and/or that the functional head can be moved by means of the force-limited drive device or by means of the force-limited drive devices essentially along a tangential plane of the main axis.

Further features are that the functional head, during the rotation around the main axis, can be guided towards the body or can be positioned with respect to the body in a remote-controlled or automated manner by the actuation of the manipulator arrangement by means of a data input arrangement, that the functional head, during the rotation around the main axis, can be guided towards the body, can be pressed on the body or can be positioned with respect to the body in a selectable position and/or with a selectable contact force in a remote-controlled or automated manner by the actuation of the manipulator arrangement by means of a data input arrangement, and that the position and/or the contact force between the functional head and the body during the rotation around the main axis can be varied in a remote-controlled or automated manner by the actuation of the manipulator arrangement by means of a data input arrangement and/or that the contact force is systemically limited, in particular that the contact force is limited by means of a pressure valve of the force-limited drive device, wherein the contact force is selectable and wherein the pressure valve is constituted as a control valve.

When the maximum contact force is exceeded, the movement element of the force-limited drive device is essentially decoupled, preferably decoupled in the direction of action, from the base element of the force-limited drive device.

According to the invention, a manipulator arrangement is provided, which can guide a functional head towards the body under the influence of increased and/or changing acceleration. This functional head can comprise components, examination and/or treatment devices such as for example an ultrasound measuring head, optical recording devices, acoustic recording devices, resistance measuring devices, an injection arrangement, a liquid analysis arrangement, a blood-taking device, an analysis device, a chemical analysis device, a radiation source, e.g. x-ray, gamma or infrared radiation, a laser source, sample-taking devices, temperature measuring devices, current measuring devices, radiation detection devices, endoscopic examination devices, devices for optical eye examination and/or further radiological, invasive or contact devices for diagnostic or therapeutic purposes.

Tasks such as for example ultrasound images of organs and/or blood vessels, blood analyses, listening to heart and/or lung function, skin resistance measurements, preparation of x-ray photographs, irradiation, heating, for example to increase the blood flow, blood flow measurement in the deeper tissue, body fat measurements, brain current measurements, cardiological measurements and further radiological, invasive or contact tasks for diagnostic or therapeutic purposes can be performed by means of the arrangement according to the invention.

The manipulator arrangement comprises one or more drive devices, which enable the movement of the functional head with respect to a base. The manipulator arrangement is constituted such that inadvertent injury to the body by the functional head and/or the manipulator arrangement is eliminated. For this purpose, a systemic safety mechanism is preferably provided, which limits the force that is applied by the manipulator arrangement to the body. For this purpose, at least one drive device of the manipulator arrangement is constituted as a flexible or sensitive drive device. Examples of such force-limited drive devices are for example arrangements which comprise actuating elements essentially free from adhesive friction such as air muscles, pneumatic actuating elements, air bellows etc. With devices of this kind, a movement element can be moved with respect to a base element by changing the length of an elastic element such as for example an air muscle or an air bellows. In addition, the device can comprise a path sensor as well as an elastic element, such as for example a spring, acting against the air muscle or the bellows. Apart from the path sensor, a force sensor is also preferably provided, which is used to control and to limit the force applied by the drive device. The actuating element can preferably be actuated pneumatically by gas pressure, in particular by air pressure. For this purpose, gas compressed by a compressor is introduced into the elastic body. This introduction of the pressure into the elastic body is regulated and/or controlled by a control valve. For the systemic limitation of the force, the gas pressure can act via a pressure relief valve in such a way that, when the desired maximum force is reached by the movement element on a body for example, the pressure relief valve opens and thus limits the pressure and the force. The pressure is directly proportional to the applied force over the area to which the pressure is applied.

Examples of the force-limited drive devices are:
  arrangements of piston-less, pneumatic actuators such as the aforementioned air bellows arrangements with the bellows cylinder or air muscle arrangements with an air muscle,
  air bellows arrangements with a bellows cylinder with a counteracting helical spring, air muscle arrangements with a counteracting spring,
the arrangement of a plurality of bellows cylinders or air muscles,
pneumatic cylinder arrangements with a pneumatic cylinder with a piston mounted free from adhesive friction, such as for example gas cylinders with graphite pistons,
gearless electric linear units with an armature mounted free from adhesive friction, air-mounted or magnet-mounted,
the arrangement of a plurality of actuators, such as pneumatic cylinders, air muscle arrangements and/or bellows arrangements as a parallel kinematic arrangement,
arrangements of pneumatic actuators with, for example, pneumatic springs, elastic elements, helical springs, guides,
combinations of one or more of the aforementioned arrangements,
etc.

The force-limited drive device, in particular a force-limited drive device with one or more of the aforementioned pneumatic actuators, can if need be comprise one or more guides. These guides serve to stabilise the movement of the movement element along of the respective degree of freedom. These guides are also suitable and/or equipped for use under the influence of increased and/or changing acceleration. Examples of such guides are linear guides, rotational guides and in particular guides which are essentially free from adhesive friction.

Apart from regulating the actuators, attention has to be paid to the friction and the inertia of the movement of the movement element in order to limit the force. In particular, actuating elements which are essentially free from adhesive friction are suitable for use as a force-limited drive device in the manipulator arrangement according to the invention.

The control of the movement of the functional head, in particular the control of the drives, preferably takes place by means of a control system. The latter is connected to the individual drives and is equipped to control or to regulate the latter. For this purpose, each axis of the drive devices can be controlled and is controllable individually or a multi-axis control can be provided. With the individual control of the axes, therefore, each linear degree of freedom can be controlled separately. Furthermore, each rotational degree of freedom can be controlled individually.

In the case of a multi-axis control, a plurality of axes are controlled simultaneously by means of one or more data input arrangements. The movement characteristics of the manipulator arrangement can be adapted by transforming the control coordinate system to an arbitrary point. The control point can preferably be placed at a contact point of the functional head with the body.

Moreover, a data input arrangement can be provided. The latter is essentially used for the input of instructions to a control system, which are relayed for example for the execution of a movement of the drives of the manipulator arrangement. Such data input arrangements can be constituted for example as joysticks, slider controls, slide valves, virtual data gloves, optical recording devices, or also by a computer and/or a computer program. The data input arrangements can preferably be disposed outside the movement device, for example in a control room. By means of the data input arrangements, the functional head can be guided in a remote-controlled or automated manner towards the body in order to perform examinations and/or treatments.

In order to improve the ease of operation, data input arrangements can also be provided with controllable or regulatable adjustment force. These input devices known by the term "force feedback" transmit signals of the forces taken up by the manipulator arrangement or the functional head to the data input arrangements. The impression of a direct "feeling" contact is thus created when the operation takes place. Furthermore, an optical recording device such as for example a camera can be provided, which conveys a video signal to a monitor. By means of this monitor, the operating person is also able to monitor the examination visually. The optical recording device is preferably connected to the base carrier element, to the base of the manipulator arrangement and/or to the fixing device. The monitor is preferably located in the region of the data input arrangement.

A manipulator arrangement is defined as a device which can move a functional head relative to a base along one or more degrees of freedom. The manipulator arrangement is controllable and/or regulatable and preferably remote-controllable. The manipulator arrangement can comprise different drive devices, which are lined up in series or in parallel. Lining-up of drive devices in series is defined as a line-up wherein a second drive device is provided on the first moving components of a first drive device. The movement of the second drive device is therefore dependent on the movement of the first drive device. The movement of the first drive device is however independent of the movement of the second drive device. The parallel provision of drive devices corresponds for example to a parallel kinematic arrangement. In parallel kinematic arrangements, the degrees of freedom are decoupled in the kinematic sense, but a coupling by means of the control may however be present in the case of multi-axis controls. The manipulator arrangement according to the invention is equipped and suitable for being used in systems with increased and/or changing acceleration.

Increased and/or changing acceleration is defined as a state of acceleration in which the manipulator arrangement experiences increased or changing acceleration forces. In particular, this means that the manipulator arrangement itself is moved. As a result of this movement, in particular as a result of the change in the movement, acceleration forces act on the manipulator arrangement and on the functional head, said acceleration forces diverging from the acceleration forces of the surroundings, e.g. forces due to gravitational acceleration. Accelerations greater than zero are regarded as increased in zero gravity space, since the acceleration the surroundings is essentially equal to zero.

Increased and/or changing acceleration is preferably regarded as a state of permanently increased acceleration, such as occurs for example in a centrifuge. Under the influence of gravitational acceleration, this would for example be an increased acceleration of approx. 1.2 G to 6 G—i.e. 1.2 to six times the acceleration due to gravity. In movement devices according to the invention, such as for example in a centrifuge, increased accelerations of up to 15 G and over may however occur. In zero gravity space, an increased acceleration would correspond for example to accelerations of approx. 0.1 G to 6 G and over. The manipulator arrangement is preferably rotated along an orbit around a main axis. The acceleration with respect to the surroundings is increased by the rotation at a certain standard distance from the main axis.

The force-limited drive device can preferably be moved along a tangential plane of the main axis. A tangential plane is defined as a plane which essentially corresponds to the normal plane on a radial vector through the main axis. The radial vector preferably lies orthogonal to the main axis. A tangential plane is therefore preferably a tangential plane of an orbit around the main axis, wherein the tangential plane preferably also runs parallel to the main axis. The direction of the radial vector essentially corresponds to the direction of the acceleration vector acting on the body or on the manipulator arrangement or to the direction of the acceleration vector that is generated by the movement device. In the case of purely linearly traversable carriages for example, the tangential plane is defined as the normal plane of the generated acceleration vector.

The direction of action of the force-limited drive device, for example for an ultrasound examination, can lie normal to the surface of the body or can also be positioned between 30° and 50° at an angle to the latter.

A device which can comprise various tools, sensors, recording devices or analysis devices is referred to as a functional head. A plurality of these components can be provided, or also just one.

According to the present invention, the functional head can be guided by the manipulator arrangement in various positions and with different contact forces towards the body and along the body. Furthermore, the position of the functional head with respect to the body can be changed with increased and/or changing acceleration. The manipulator arrangement preferably comprises six degrees of freedom. The movement of the drive devices preferably takes place in a position-controlled manner. The movement of the force-limited drive device preferably in a force-controlled manner.

Furthermore, the contact force or the pressing force of the functional head on the body can be held at a constant or specific value by means of the manipulator arrangement according to the invention and the force-limited drive device. The value can be inputted in a remote-controlled manner for example via a data input arrangement or can be preselected automatically by a program. The contact or pressing force is preferably independent or decoupled from the movement of the movement device and the acceleration acting on the body and/or the manipulator arrangement. The contact force can be changed, selected and/or limited via the data input arrangement. In order to control the movement, in particular the rotation of the functional head, provision can be made such that the point of rotation of the functional head lies at the point of contact of the functional head with the body. The control can be assisted, if need be, by controlling the linear drives or can be performed as a multi-axis control.

According to the invention, the manipulator arrangement is provided, if appropriate, on a movement device. Examples of movement devices are flight simulators, centrifuges, centrifuges with a traversable carriage, linearly traversable carriages, medical centrifuges, training centrifuges etc. Practical applications of the manipulator arrangements in combination with a movement device are for example the examination of persons in one-arm centrifuges or the examination of persons in linearly traversable devices, for example for longitudinal dynamic simulation. Furthermore, the movement device according to the invention can be provided in zero gravity space, for example in space stations or spaceships. Especially in the case of long periods of time spent by persons or animals in space, a simulation of accelerations, for example by means of a centrifuge, is necessary in order to prevent muscular atrophy and weakening of the skeleton. For this purpose, one or more nacelles, for example, are disposed rotatably around a main axis. By rotation of the individual nacelles at a certain standard distance, the persons positioned in the nacelles experience a certain acceleration. By the provision of training devices such as for example an ergometer, training units can thus be performed in zero gravity space under the influence of normal, changing or increased acceleration. Such medical centrifuges or also training centrifuges can also be used, especially for scientific purposes, on earth under the influence of gravitational acceleration. These movement devices also correspond to a use of the present invention.

The invention will be described below in greater detail with the aid of specific, diagrammatically represented examples of embodiment.

DESCRIPTION OF THE INVENTION

Figure 1:
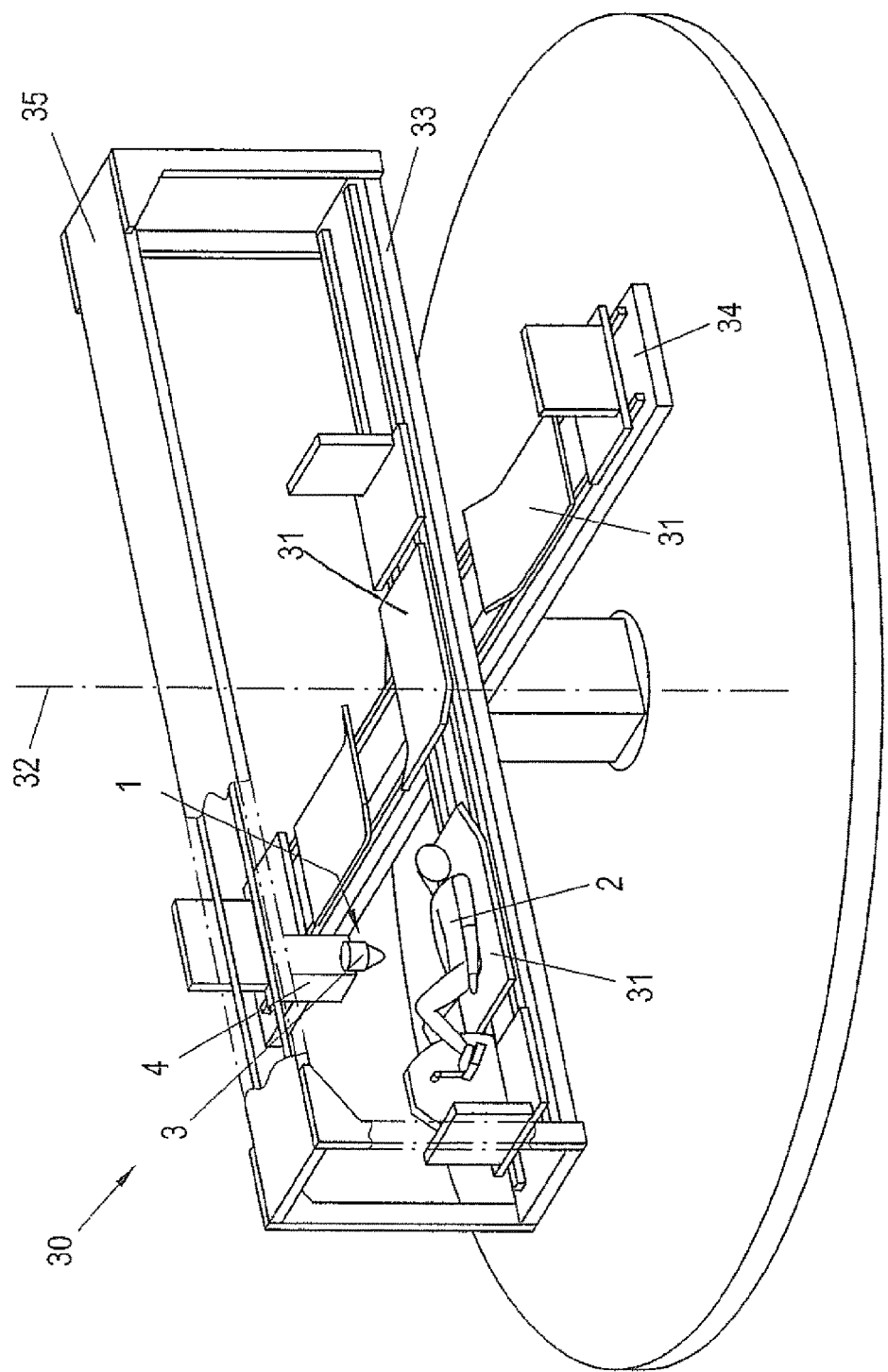
FIG. 1 shows a diagrammatic oblique view of a movement device according to the invention comprising a manipulator arrangement according to the invention.

FIG. 1 shows an arrangement of a movement device 30, comprising a plurality of fixing devices 31, which are disposed rotatably around a main axis 32. The arrangement corresponds to a possible movement device of a medical centrifuge or a training centrifuge for use in the zero gravity state or under the influence of gravitational acceleration.

Figure 2:
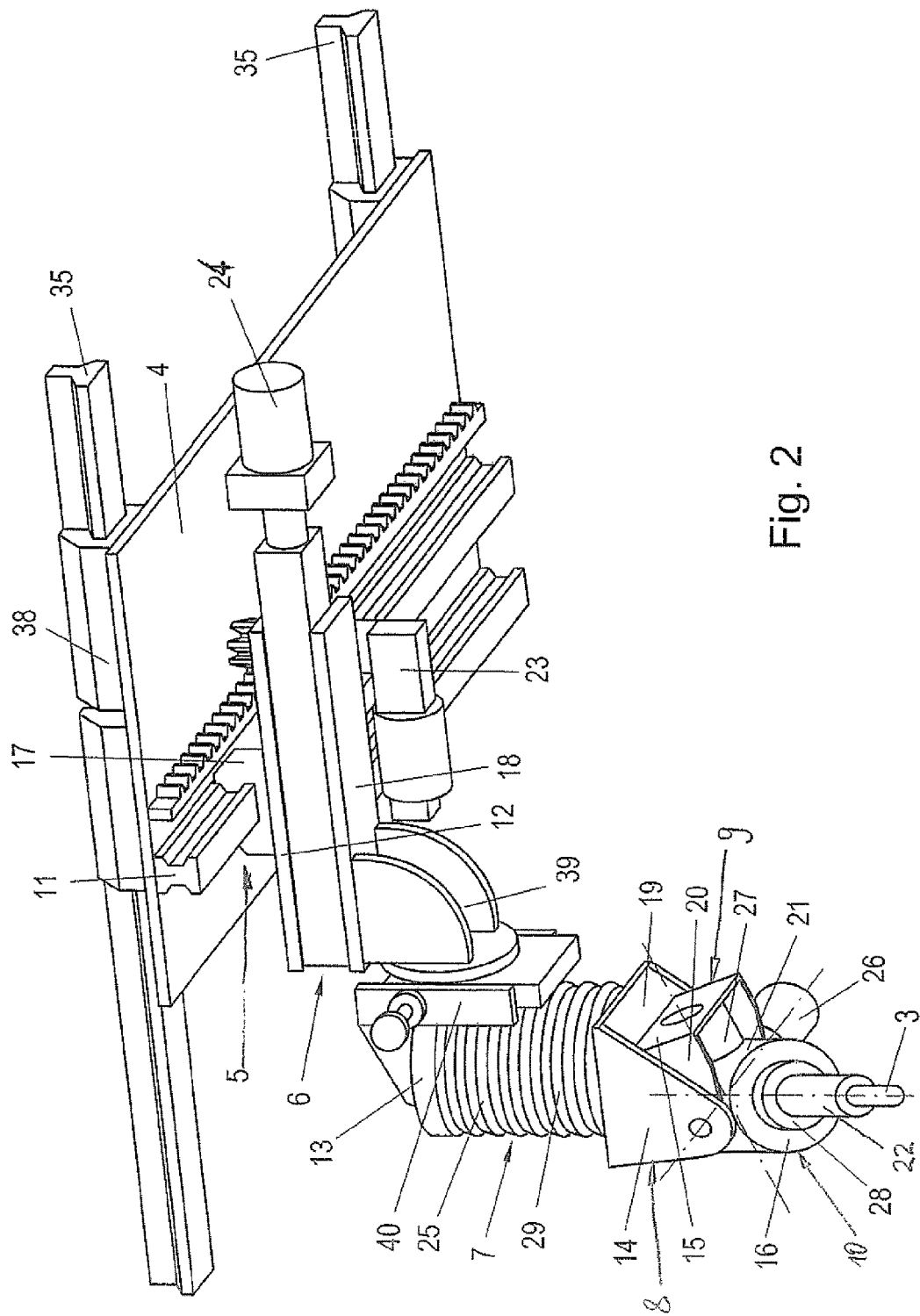
FIG. 2 shows a possible embodiment of a manipulator arrangement.

A body 2 of a test subject is lying on fixing device 31. In the present embodiment, fixing device 31 is disposed displaceable along a first carrier element 33. By rotation of first carrier element 33 around main axis 32, body 2 experiences an increased acceleration. This is made up of the main acceleration, usually gravitational acceleration, and the radial acceleration. During use in the zero gravity state, the basic acceleration is essentially zero. The magnitude of the radial acceleration is essentially dependent on the angular velocity and the standard distance from main axis 32. In order to be able to vary the resultant acceleration on the body, at least one, preferably all acceleration devices 31, is constituted displaceable in the present embodiment, wherein the direction of the displacement essentially runs radially with respect to main axis 32 and/or along first or second carrier element 33, 34. A base carrier element 35 is rigidly connected to first carrier element 33. In the present embodiment, said base carrier element comprises rail-shaped sections on which base 4 of manipulator arrangement 1 is disposed so as to be linearly displaceable. This displacement of base 4 on base carrier element 35 is preferably used for the rough adjustment and the positioning of manipulator arrangement 1 in the region of body 2 of the person. Functional head 3 is disposed movably by means of drive devices on base 4 of manipulator arrangement 1. The representation of manipulator arrangement 1 in FIG. 2 is very simplified and schematised. For the performance of treatments or examinations on the human or animal body, functional head 3 of manipulator arrangement 1 can be guided towards body 2 of the person by means of control system 36 (not represented here). This takes place for example via a data input arrangement. If need be, the rotation of the movement device can also be controlled by means of the same control system.

Movement device 30 of FIG. 1 corresponds to a diagrammatic representation of a device for the medical examination or treatment of human or animal bodies under the influence of increased or changing acceleration. For this purpose, a plurality of fixing devices 31 are provided on a first and second carrier element 33, 34 disposed in the form of a cross. Performance or loading tests, for example, can be carried out under increased acceleration forces on such a movement device. Fixing devices 31 are preferably connected in a movable manner to the first and the second carrier element. As a result of the movement of the fixing device with body 2 of the person, the resultant acceleration force acting on the person can be reduced without influencing the test on the remaining three fixing devices. The movement device preferably rotates at a constant angular velocity around main axis 32. The resultant acceleration acting on body 2 can be changed by selecting the distance of body 2 from this main axis 32.

In order to be able to carry out examinations or treatments on body 2 under these conditions, functional head 3 of manipulator arrangement 1 is provided so as to be movable on base carrier element 35. By means of a control system and data input arrangements, functional head 3 can be guided by means of the manipulator arrangement towards body 2. For example, blood samples can be taken and analysed, ultrasound images of the organs can be taken under increased loading or further tests can be carried out by means of functional head 3.

As has been mentioned, it is absolutely essential for this purpose that inadvertent injury to person 2 due to functional head 3 is eliminated. For this purpose, manipulator arrangement 1 according to the invention comprises at least one force-limited drive device, which has a mobile degree of freedom which is force-limited, i.e. flexible, sensitive or "compliant".

FIG. 2 shows a detailed oblique view of a manipulator arrangement 1 according to the invention and parts of movement device 30. Base 4 is connected in a rail-like manner to base carrier element 35. For this purpose, guide elements 38 of base 4 are provided so as to be linearly displaceable on rail-shaped bodies of base carrier element 35. Base 4 is therefore preferably displaceable with respect to base carrier element 35 and disposed in the desired position in an arrestable manner. In the present embodiment, this displacement is used for the rough positioning of manipulator arrangement 1 in the region of body 2. A first drive device 5 is provided on base 4. Said drive device comprises a first base element 11, a first movement element 17 and a first drive 23 for moving first movement element 17 with respect to first base element 11. In the present embodiment, the first drive device is constituted essentially as a linear axis. For this purpose, guide elements of first movement element 17 engage in grooves, preferably in undercut grooves of first base element 11 constituted rail-shaped. First drive 23 is provided for the movement, said first drive being equipped to move first movement element 17 with respect to first base element 11. In the present embodiment, this is constituted by a toothed rack provided on first base element 11 and a cogwheel for engaging in the toothed rack, said cogwheel being driven by a first drive 23 and being provided on first movement element 17. First drive 23 can preferably be controlled and/or regulated by control system 36. If need be, two rail-shaped base elements 11 running in parallel and a plurality of guide elements can be provided to improve the stability.

By means of first drive device 5, therefore, a first drivable degree of freedom is provided for the movement of functional head 3 with respect to base 4. A second drive device 6 is provided on first movement element 17. Said second drive element comprises a second base element 12, which is connected essentially rigidly to first movement element 17. Furthermore, second drive device 6 comprises a second drive 24 for moving second movement element 18 with respect to second base element 12. By means of second drive device 6, therefore, a further drivable degree of freedom is provided for moving functional head 3 with respect to base 4. In the present embodiment, second drive device 6 is constituted as a linear axis. This enables a movement along a linear degree of freedom, said movement being controlled and/or regulated by control system 36. Second movement element 18 is thus moved linearly with respect to second base element 12 by means of drive 24. As a result of the present arrangement of the two linear axes of first and second drive device 5 and 6, functional head 3 can thus be moved two-dimensionally along a plane. The movement direction of first drive device 5 and the movement direction of second drive device 6 preferably run essentially orthogonal to one another. In this embodiment, both movement devices preferably run in a normal plane of the main axis.

Third drive device 7 is provided on second movement element 18 of second drive device 6. In the present embodiment, the connection of the third drive device 7 to second movement element 18 takes place by means of a swivelling device 39 and a feed device 40. Swivelling device 39 and feed device 40 are essentially rigid connections which, by the operation of a bolt for example, are used for the rough adjustment of the position of third drive device 7 with respect to second drive device 6. By means of swivelling device 39, functional head 3 and third drive device 7 can be swivelled away, for example to facilitate the entry and exit of the person. Feed device 40 is used for the rough distance adjustment of the functional head with respect to body 2 of the person. Swivelling device 39 and feed device 40 are preferably rigid and not driven during normal operation. Alternatively, however, the third drive device, in particular the third base element, can also be connected rigidly to the second movement element. In this alternative embodiment, the swivelling device and/or the feed device are dispensed with.

In the present embodiment, third drive device 7 is constituted as a force-limited drive device 29. It comprises a third base element 13 and a third movement element 19 and a third drive 25. Third drive 25 for moving third movement element 19 with respect to third base element 13 is constituted as a force-limited drive. For this purpose, any force-limited drive is in principle suitable that permits a force limitation in systems with increased or changing acceleration.

In the embodiment represented, the movement direction of third drive device 7 or of force-limited drive device 29 runs orthogonal to the movement direction of first drive device 5 and orthogonal to the movement direction of second drive device 6. A spatial, preferably Cartesian movement of functional head 3 with respect to base 4 is thus enabled by the three driven degrees of freedom of first, second and third drive device 5, 6, 7. The movement direction of the force-limited drive device preferably runs normal to the direction of the vector of the radial acceleration and therefore in a tangential plane of the main axis. The magnitude of the acceleration caused by the rotation of functional head 3 and manipulation arrangement 1 around main axis 32 of movement device 30 thus has no influence or only a slight influence on the mass forces in force-limited drive device 29. In a preferred embodiment, the movement direction of force-limited drive device 29 runs parallel to main axis 32 of movement device 30.

It is however perfectly in accordance with the idea of the invention to select the movement direction of force-limited drive device 29 freely with respect to the acceleration forces or freely with respect to main axis 32.

Fourth drive device 8 is provided on third drive device 7, in particular on third movement element 19. Said fourth drive device in turn comprises a fourth base element 14 and a fourth movement element 20, wherein fourth movement element 20 can be driven and rotated with respect to fourth base element 14 by means of a fourth drive 26.

Fourth drive device 8 thus enables a first driven rotational degree of freedom. A fifth drive device 9 is provided on fourth drive device 8, in particular on fourth movement element 20. Said fifth drive device comprises a rotational degree of freedom of fifth movement element 21 with respect to fifth base element 15, said rotational degree of freedom being driven by a fifth drive 27. Provided on fifth drive device 9 is a sixth drive device 10, which comprises a sixth drive 28 which enables a rotation of sixth movement element 22 with respect to sixth base element 16. A gimbal-mounted rotatability of functional head 3 is enabled by the lining-up of fourth, fifth and sixth drive devices 8, 9, 10. Furthermore, fourth base element 14 is connected rigidly to the third movement element, fifth base element 15 rigidly to fourth movement element 20, sixth base element 16 rigidly to fifth movement element 21 and sixth movement element 22 rigidly to functional head 3.

In the present embodiment, therefore, six drivable, controllable and/or regulatable drive devices are lined up in series. Three of the drive devices permit a movement along linear axes and three of the drive devices permit a rotation around rotational axes. Two successive rotational axes or linear axes preferably lie orthogonal to one another in each case. The force-limited drive device is preferably force-controlled, the other drive devices preferably being path-controlled or position-controlled. The contact force of the force-limited drive device can furthermore be selected and/or limited.

Figure 3:
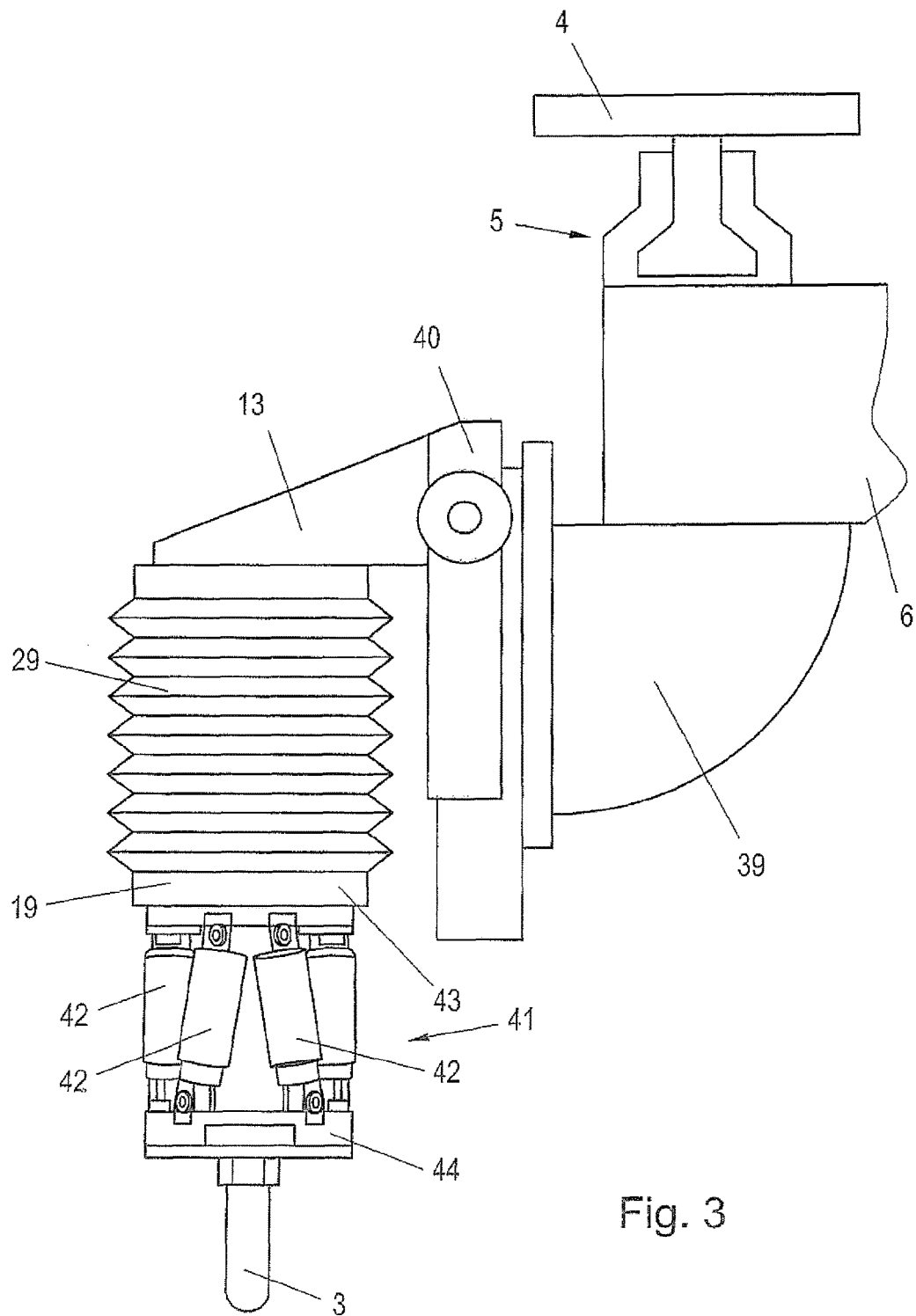
FIG. 3 shows a further possible embodiment of the manipulator arrangement, in particular a detail of the force-limited drive device.

FIG. 3 shows a further embodiment of a part of the manipulator arrangement according to the invention. In the case of the latter, functional head 3 is disposed so as to be movable along a plurality of degrees of freedom by means of a plurality of drive devices. The functional head is rigidly or rotatably connected or coupled to movement element 44 of a parallel kinematic device. Parallel kinematic device 41 comprises a base element 43, a plurality of drives 42 and a movement element 44, which can be moved with respect to the parallel kinematic device/base element 43 by means of drives 42. Drives 42 are preferably constituted as linear axes, for example as pneumatic or hydraulic cylinders. They are connected to a control system and can be controlled preferably separately from one another or jointly. An inclination of movement element 40 with respect to base element 43 can be achieved by the differing change in length of individual drives. Parallel movements of movement element 44 with respect to base element 43 are also possible by a suitable control of drives 42. A spatial movement of functional head 3 is thus enabled by the suitable control of drives 42. The mode of functioning of the parallel kinematic device corresponds, for example, to that of a hexapod or that of a tripod.

In the present embodiment, base element 43 is provided on force-limited drive device 29. As in FIG. 2, the latter is constituted as a linearly acting force-limited drive device. It comprises a third base element 13 and a third movement element 19, wherein third movement element 19 is rigidly connected to base element 43. Third base element 13 is connected, as in FIG. 2, to a feed device 40 and a swivelling device 39. The mode of functioning with swivelling device 39 and feed device 40 essentially corresponds to the action of the equivalent parts in FIG. 2. The remaining structure of the embodiment also essentially corresponds to the structure from FIG. 2. Thus, the swivelling device is provided rigid on a second drive device, which comprises a second base element 12, a second movement element 18 and a second drive 24 for moving the second movement element with respect to the second base element. Second base element 12 is connected to a first drive device 5. In terms of its structure, the latter also corresponds to the first drive device from FIG. 2. First drive device 5 is provided on base 4. This base 4 can, as represented in FIG. 1, be connected displaceably or fixedly to movement device 30.

The present embodiment of FIG. 3 differs from the embodiment of FIG. 2 essentially by the configuration of the drive devices for moving the functional head with respect to force-limited drive device 29. Whereas in FIG. 2 a rotation of a plurality of elements around axes essentially orthogonal to one another is enabled, a parallel kinematic device is used for the inclination and the spatial movement of the functional head 3 according to the embodiment of FIG. 3.

Figure 4:
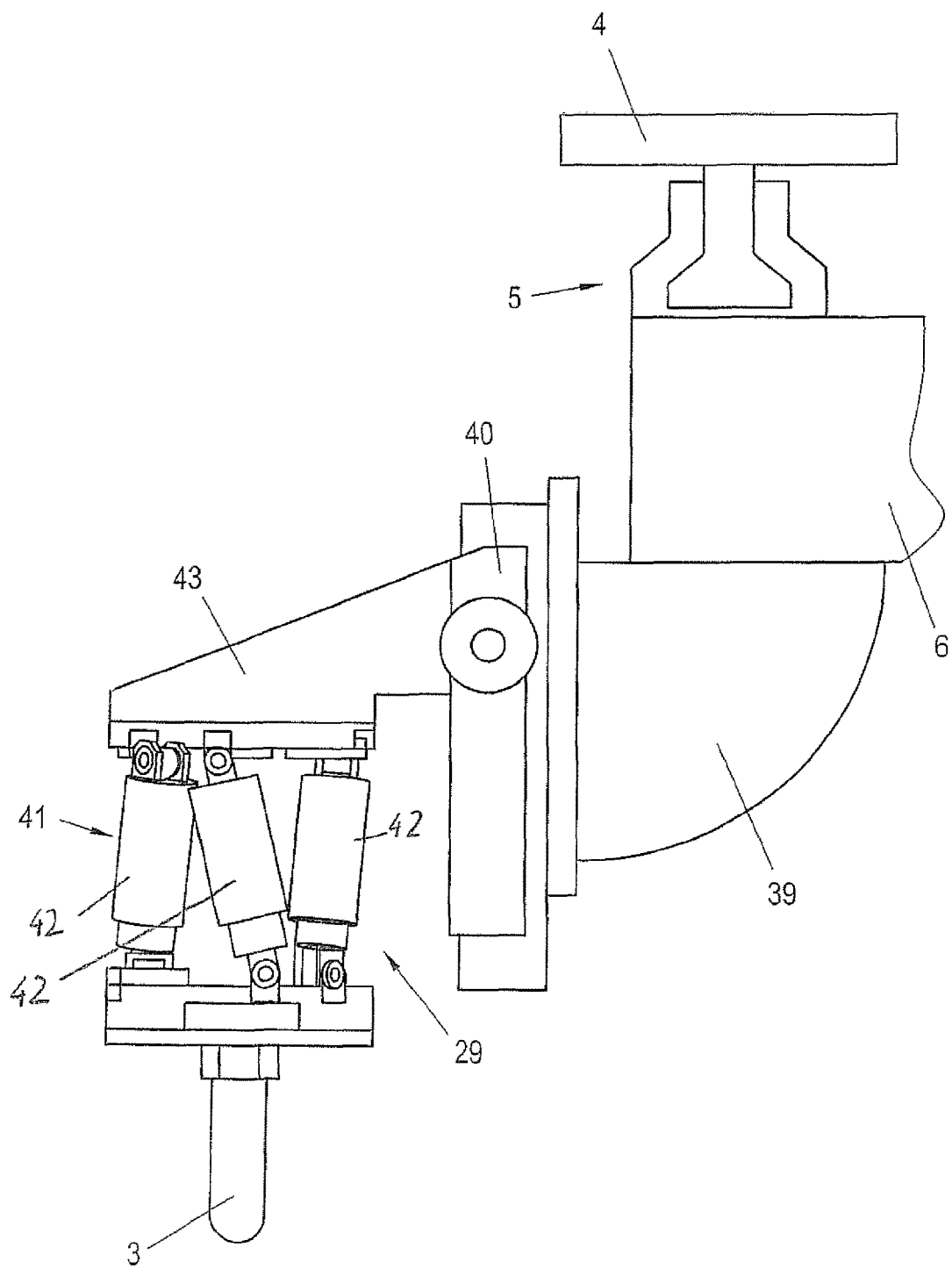
FIG. 4 shows a further embodiment of a manipulator arrangement with a force-limited drive device.

FIG. 4 shows a further embodiment of the device according to the invention. A first drive device 5 and a second drive device 6 are again provided on a base 4. A swivelling device 39 and a feed device 40 are again provided on second drive device 6. Feed device 40 is rigidly connected to base element 43. The structure of the manipulator arrangement corresponds to the structure of the embodiment of FIGS. 2 and 3 in respect of first drive device 5, second drive device 6 as well as swivelling device 39 and feed device 40. According to the embodiment according to FIG. 4, force-limited drive device 29 is constituted as a parallel kinematic device 41. Each individual drive 42 of parallel kinematic device 41 can be constituted force-limited or sensitive. As an alternative to this, whole parallel kinematic device 41 can also be constituted force-limited as a unit. The embodiment of FIG. 4 thus corresponds essentially to the embodiment of FIG. 3, wherein the arrangement of the force-limited drive device with a parallel kinematic device is united in a force-limited parallel kinematic device.

Figure 5:
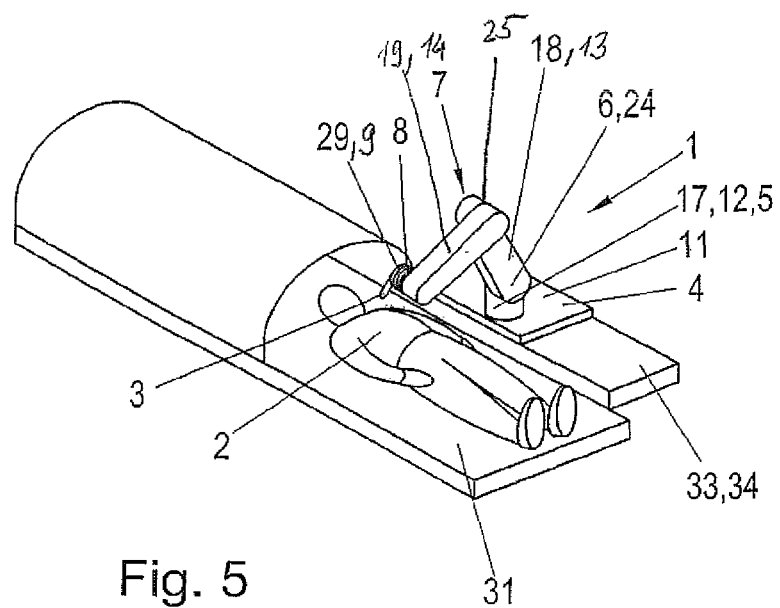
FIG. 5 shows a possible manipulator arrangement with parts of a movement device in an oblique view.

FIG. 5 shows a possible further embodiment of the manipulator arrangement according to the invention in a schematised representation. Fixing device 31 for accommodating or fixing a body 2 is disposed similar to the fixing device from FIG. 1. For example, the vertical body axis runs radially, the head pointing in the direction of main axis 32. The acceleration component that is generated by rotation of fixing device 31 around main axis 32 also runs essentially following the vertical body axis. In the present embodiment, manipulator arrangement 1 comprises a base 4, which is disposed displaceability or fixedly on first or second carrier element 33, 34 of the movement device. Furthermore, the manipulator arrangement comprises a first drive device 5 with a first base element 11 which is connected fixedly to base 4. First movement element 17 can be moved or driven with respect to first base element 11 by means of a first drive 23. The movement takes place by rotation around an axis which runs essentially parallel to main axis 32. A second base element 12 is provided on first movement element 17. A second movement element 18 can be moved with respect to this second base element 12 by means of a second drive 24. Together, the components produce second drive device 6. This drive is also a rotary drive, wherein the axis of the rotation runs essentially normal to the axis of first drive device 5. Second movement element 18 is constituted arm-shaped and, in a region distant from the second drive, is connected to third drive device 7. The latter in turn comprises a third base element 13, which is connected rigidly to second movement element 18. Furthermore, the third drive device comprises a third drive 25, which can rotate an arm-shaped third movement element 19 around a rotational axis, which runs essentially normal to the rotational axis of second drive device 6. Third base element 19 and the second movement element can be constituted in one piece in a preferred embodiment.

A fourth drive device 8 is provided on third drive device 7, in particular on third movement element 19. A fifth drive device 9, which is constituted as a force-limited drive device 29, is provided on fourth drive device 8.

Figure 6:
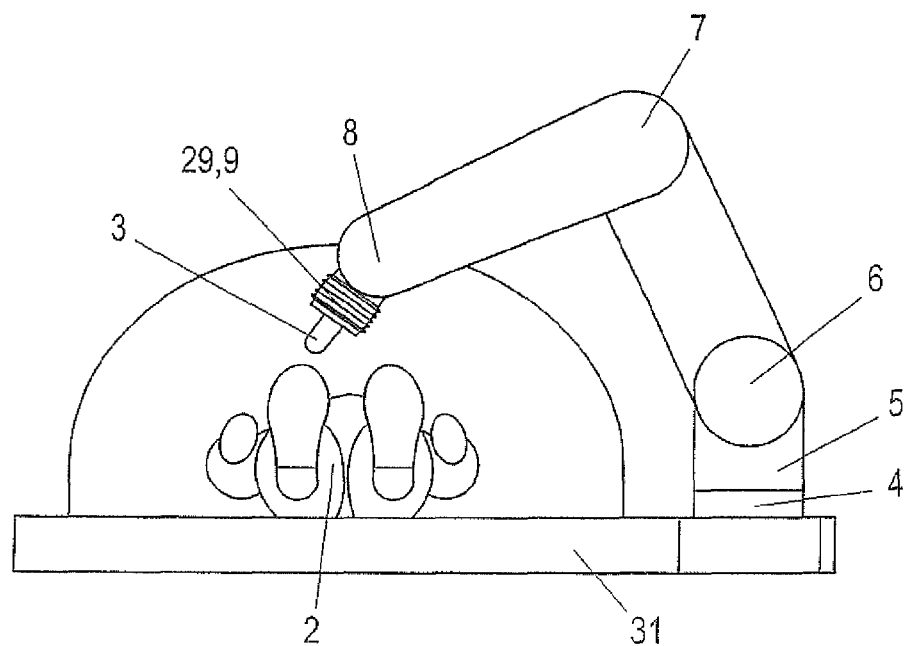
FIG. 6 shows the same arrangement as FIG. 5, but in another view.

FIG. 6 also shows the same the arrangement as FIG. 5 with a base 4, on which first drive device 5 is provided rotatably. Second drive device 6 is provided on first drive device 5, third drive device 7 is provided on second drive device 6, fourth drive device 8 is provided on third drive device 7 and fifth drive device 9 is provided on fourth drive device 8, said fifth drive device being constituted as a force-limited drive device 29. Functional head 3 is provided on force-limited drive device 29 in FIGS. 5 and 6. The functional head can be guided towards body 2 of the person by the movement of manipulator arrangement 1, in particular the movement of movement elements 17, 18, 19, 20 by means of drives 23, 24, 25, 26, 27 and 29.

Figure 7:
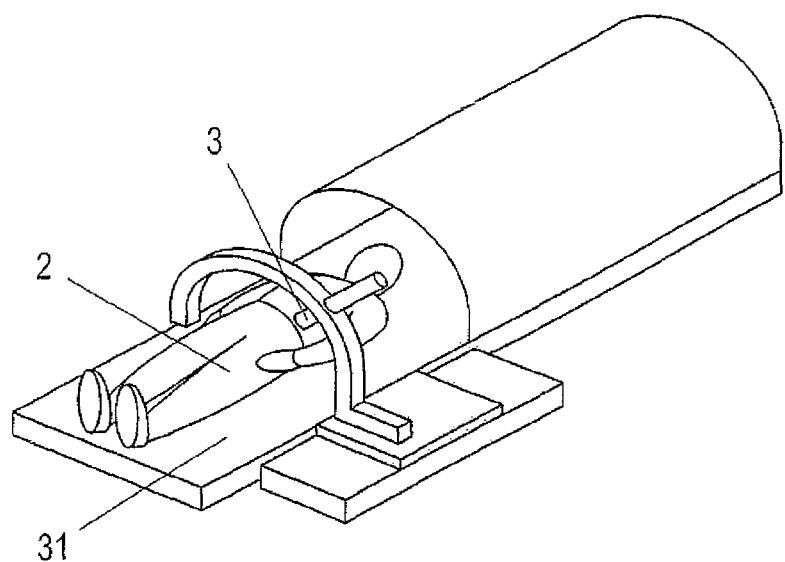
FIG. 7 shows a further embodiment of a possible manipulator arrangement with parts of a movement device in a diagrammatic oblique view.
Figure 8:
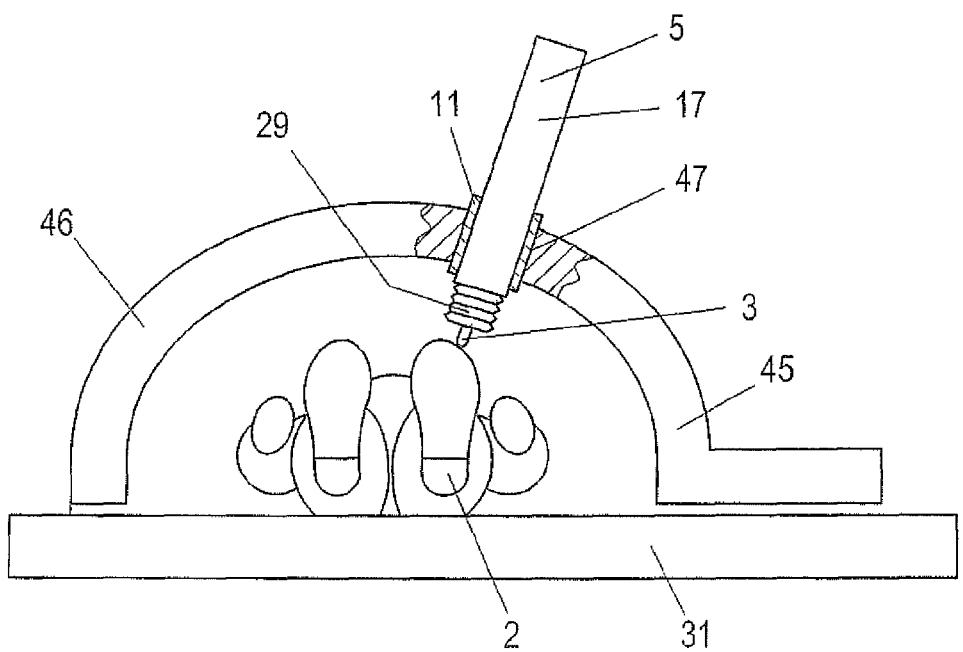
FIG. 8 shows the same arrangement as FIG. 7, but in another view.

FIG. 7 and FIG. 8 each show different views of a further embodiment of the inventive arrangement of a manipulator arrangement and a movement device. Once again, the position of fixing device 31 for body 2 corresponds to the position from FIG. 1. The manipulator arrangement for moving functional head 3 towards body 2 of the person comprises an arc-type drive 45. Arc-type drive 45 comprises a base element 46, which extends in the shape of an arc around or over body 2 of the person. Disposed displaceably on the latter is movement element 47 of the arc-type drive, wherein functional head 3 points essentially inwards in the direction of body 2.

A first drive device 5 is provided on movement element 47 of arc-type drive 45. Said first drive device comprises a first base element 11 and a first movement element 17. The latter can be moved linearly with respect to the first base element. The direction of the linear movement essentially follows the radial direction of the instantaneous position along base element 46 of the arc-type drive.

Force-limited drive device 29 is provided in the extension of first movement element 17. Provided on said drive device is functional head 3, which points in the direction body 2 and can be fed towards and pressed on the latter by means of the manipulator arrangement.

Figure 9:
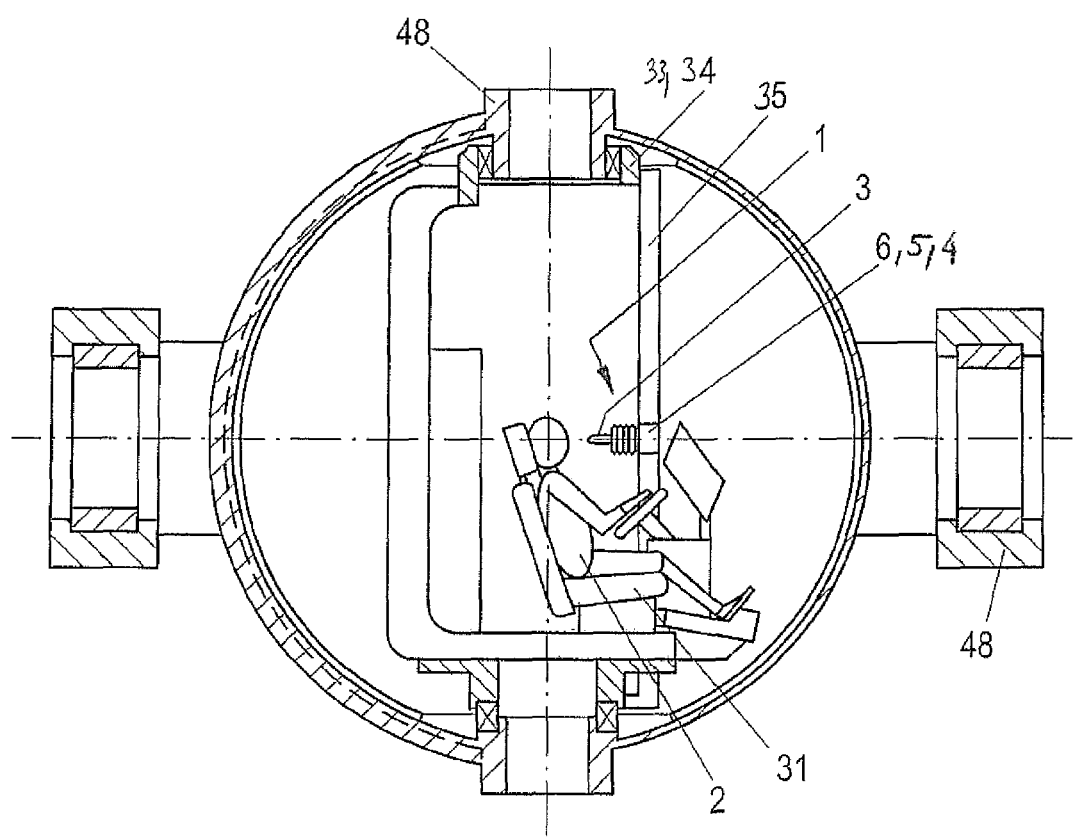
FIG. 9 shows a further embodiment of the manipulator arrangement and parts of a movement device.

FIG. 9 shows a further application of the manipulator arrangement according to the invention and a movement device according to the invention.

Fixing device 31 for body 2 of a person is provided in or on a simulator cabin. According to the prior art, the simulator cabin is provided for example on a one-arm or multi-arm centrifuge. For this purpose, the simulator cabin is mounted rotatably and drivably by means of one or more roll rings 48. The outermost roll ring is preferably connected to the arm of a centrifuge. According to the prior art, this arm is rotated around a main axis 32. The simulator cabin is disposed at a certain standard distance from rotational axis 32. A manipulator arrangement 1 is in turn provided in the simulator cabin, preferably in the region of fixing device 31. In the present embodiment, said manipulator arrangement is represented diagrammatically. The manipulator arrangement again comprises a functional head 3, which can be fed towards body 2 of the person by means of a plurality of drivable drive devices. At least one drive device is constituted as a force-limited drive device 29.

Functional head 3 is linearly traversable by means of a first drive device 5. The functional head can be linearly traversed in a further direction by means of a second drive device 6. A manipulator arrangement according to the present embodiment of FIG. 9 or according to an embodiment of FIG. 1 to 8 is preferably provided on the base.

According to a further embodiment, a plurality of drive devices are constituted as force-limited drive devices. This embodiment corresponds to the embodiment of FIG. 2, wherein, in addition to the third drive device, the second drive device is also constituted as a force-limited drive device.

In addition to the third drive device of FIG. 2, the second and the first drive device are also constituted as force-limited drive devices according to a further embodiment.

According to a further embodiment, the drive devices whose movement axes each lie essentially in a tangential plane of the main axis are constituted as force-limited drive devices. For example, the movement axes of the first and the third drive device each lie in a tangential plane of the main axis in FIG. 2.

An exemplary use of the manipulator arrangement according to the invention and the movement devices according to the invention for an ultrasound examination with increased acceleration will be discussed further in the following. For the examination or treatment of a body 2, the body is fixed to fixing device 31 or is placed on the latter. Fixing device 31 is connected to a first carrier element 33 or to a second carrier element 34. While the movement device is stationary, the person lies or sits on fixing device 31 and if need be straps himself in on the latter. In the case of one-arm centrifuges, flight simulators and/or simulator cabin, as represented for example in FIG. 9, the person sits in a simulated cockpit of an aircraft. In the movement device according to FIG. 1, the person lies on the fixing device which, as the case may be, comprises ergometer elements or other devices for loading the human body.

The manipulator arrangement is subsequently brought into the region of body 2 of the person. This takes place for example by displacement of base 4 along base carrier element 35 or by the remote-controlled or automated operation of the drive devices, for example of first drive device 5. Functional head 3 is guided to the desired point of the body and pressed thereon.

For the ultrasound examination, the functional head is constituted as an ultrasound head. The latter is placed against the body in the rest position of the movement device, in such a way that the desired image is displayed on an evaluation unit, for example in a control room or on a mobile device. The movement of the movement device is started in this basic position, in which the functional head is guided by the manipulator arrangement to the desired point of body 2. In the case of the embodiment of FIG. 1, first and second carrier element 33, 34 are rotated around main axis 32. In other embodiments, for example in the embodiment of FIG. 9, the represented simulator cabin is also rotated around a main axis 32 via a main arm (not represented). As a result of the increased and/or changing acceleration, the considered organs of body 2 or the body itself possibly also change position. In order to obtain the desired image, the functional head can be moved by means of the manipulator arrangement. This takes place by the remote-controlled or automated movement of the drive devices. A control system 36 and a data input arrangement 37 are provided for controlling the movement of the functional head and the manipulator arrangement. For example, another person can control the movement of the functional head with respect to body 2 from a control room by means of elements such as joysticks, slider controls, data gloves, etc. Furthermore, the functional head according to the manipulator arrangements of FIGS. 2 to 8 can be driven and moved along a plurality of degrees of freedom. Thus, on the one hand, the angle of the functional head with respect to the body can be changed via rotational degrees of freedom. On the other hand, the position of the functional head with respect to the body can be changed via translatory degrees of freedom. In order to examine a different point of the body, the functional head can be raised from body 2 and guided to another point of the body and pressed thereon by means of the data input arrangement and the control of the drive devices.

Inadvertent injury to the body is prevented by the force-limited drive device. The drive device whose degree of freedom or direction of action enables pressure to be exerted on body 2 is preferably constituted force-limited. For example, this is the linear degree of freedom whose direction of action runs normal to the surface of the body. If the functional head is guided towards body 2 by remote control, this takes place with a pre-adjusted or selected force and a pre-adjusted or selected maximum force. Even in the case of a malfunction of the drive devices that are not force-limited, inadvertent injury to the body by the functional head is prevented, since the decisive force component of the kinematic arrangement is constituted force-limited.

To perform other examinations or treatments, the functional head can comprise components, examination and/or treatment devices such as for example an ultrasound measuring head, optical recording devices, acoustic recording devices, resistance measuring devices, an injection arrangement, a liquid analysis arrangement, a blood-taking device, an analysis device, a chemical analysis device, a radiation source, e.g. x-ray, gamma or infrared radiation, a laser source, sample-taking devices, temperature measuring devices, current measuring devices, radiation detection devices and/or further radiological, invasive or contact devices for diagnostic or therapeutic purposes. The movement of the functional head and the performance of the examination or the treatment takes place in the manner described.

The movement devices represented in FIG. 1 and FIG. 9 are exemplary movement devices. The manipulator arrangement according to the invention is provided on the latter. The manipulator arrangement according to the invention comprises a plurality of drive devices, wherein at least one of these drive devices is constituted as a force-limited drive device. The manipulator arrangement comprises a functional head which is equipped for contact and/or invasive examination or treatment of the animal or human body. For this purpose, the functional head can preferably be traversed along a plurality of translatory degrees of freedom and rotated around a plurality of rotational degrees of freedom. The various embodiments of the degrees of freedom of FIGS. 2, 3 and 4, in particular the embodiment of the force-limited drive device with a cardan-shaft drive device, a parallel kinematic arrangement or a force-limited parallel kinematic arrangement, can also be disposed on the manipulator arrangements represented in FIGS. 5 to 8. Thus, for example, the force-limited parallel kinematic arrangement of FIG. 4 can be disposed on the robot arm of FIG. 6. For example, the parallel kinematic arrangement with an independent, force-limited drive device disposed thereon can also be provided on the movement element of arc-type drive 47 of FIGS. 7 and 8. Combinations of FIGS. 2, 3, 4 with the various embodiments of the manipulator arrangements in FIGS. 2 and 5 to 8 also correspond to the idea of the invention. The manipulator arrangements according to FIGS. 2 to 8 and/or the general description part can be fitted on the movement devices of, for example, FIGS. 1 to 9 or of the general description part.

LIST OF REFERENCE NUMBERS 1 manipulator arrangement
2 body
3 functional head
4 base
5 first drive device (Y)
6 second drive device (X)
7 third drive device (Z)
8 fourth drive device
9 fifth drive device
10 sixth drive device
11 first base element
12 second base element
13 third base element
14 fourth base element
15 fifth base element
16 sixth base element
17 first movement element
18 second movement element
19 third movement element
20 fourth movement element
21 fifth movement element
22 sixth movement element
23 first drive
24 second drive
25 third drive
26 fourth drive
27 fifth drive
28 sixth drive
29 force-limited drive device
30 movement device
31 fixing device
32 main axis
33 first carrier element
34 second carrier element
35 base carrier element
36 control system
37 data input arrangement
38 guide element
39 swivelling device
40 feed device 41 parallel kinematic device
42 drive-parallel kinematic device
43 base element parallel kinematic device
44 movement element parallel kinematic device
45 arc-type drive
46 base element arc-type drive
47 movement element arc-type drive
48 roll ring

The invention claimed is:

1. A movement device being a centrifuge, a medical centrifuge or a training centrifuge, the movement device comprising:
a carrier element;
at least one fixing device for accommodating, laying on and/or fixing a human or animal body, said at least one fixing device disposed on said carrier element being disposed rotatably around a main axis;
a manipulator configuration being suitable for contact and/or invasive examination or treatment of the human or animal body under an influence of permanently increased and/or changing acceleration, wherein said manipulator configuration having a functional head, wherein the increased and/or the changing acceleration being defined as a state of acceleration in which said manipulator configuration experiences increased or changing acceleration forces, and as a result of movement and as a result of a change in the movement, the acceleration forces act on said manipulator configuration and on said functional head, and the acceleration forces diverging from acceleration forces of surroundings; and
said manipulator configuration further containing a base and drive devices and at least one of said drive devices is a force-limited drive device having a pressure valve, wherein said functional head being movable relative to said base along a plurality of degrees of freedom movable by said drive devices, wherein a position and/or a contact force of said functional head touching the body is variable with respect to the body under an influence of the increased and/or changing acceleration, wherein a contact force is systemically limited, whereby inadvertent injuries to the body due to said functional head and/or said manipulator configuration are prevented.

2. The movement device according to claim 1, wherein said movement device is constituted as a flight simulator, as a one-arm centrifuge, as a centrifuge with a traversable carriage, as a centrifuge with a traversable heave carriage, as a training centrifuge for use under zero gravity, as a medical centrifuge with a plurality of nacelles disposed rotatably around the main axis.

3. The movement device according to claim 1, further comprising a base carrier element coupled or connected to said carrier element, said base carrier element being connected, coupled or capable of being connected to said base of said manipulator configuration.

4. The movement device according to claim 1, wherein said functional head can be moved by said force-limited drive device along a tangential plane of the main axis.

5. The movement device according to claim 1, further comprising a data input configuration, said functional head, during a rotation around the main axis, can be guided towards the body and/or can be positioned with respect to the body in a remote-controlled or automated manner by an actuation of said manipulator configuration by said data input configuration.

6. The movement device according to claim 1, further comprising a data input configuration, said functional head, during a rotation around the main axis, can be guided towards and pressed on the body and/or can be positioned with respect to the body in a selectable position and/or with a selectable contact force in a remote-controlled or automated manner by actuation of said manipulator configuration by said data input configuration.

7. The movement device according to claim 1, further comprising a data input configuration, a position and/or a contact force between said functional head and the body during a rotation around the main axis can be varied in a remote-controlled or automated manner by actuation of said manipulator configuration by said data input configuration.

8. The movement device according to claim 1, wherein said force-limited drive device has a pressure valve, and a contact force is systemically limited by said pressure valve of said force-limited drive device.

9. the movement device according to claim 8, wherein the contact force is selectable and that said pressure valve is constituted as a control valve.

10. The movement device according to claim 1, wherein said force-limited drive device has at least one component selected from the group consisting of a piston-less pneumatic actuator, at least one air muscle configuration, at least one air bellows configuration, at least one pneumatic cylinder configuration with pneumatic cylinders with pistons mounted generally free from adhesive friction, at least one gearless electric linear unit with armatures mounted generally free from adhesive friction and at least one guide.

11. The movement device according to claim 1, wherein said drive devices contain at least one component selected from the group consisting of linear axis, a rack-and-pinion drive, a parallel kinematic drive, a hexapod, a tripod, a robot arm, a rotary drive, a cardan-shaft drive and a Cartesian drive.

12. The movement device according to claim 1, wherein said drive devices each have a base element, a movement element and a drive for moving said movement element with respect to said base element along the degreee or respective degrees of freedom and that said drive devices are lined up in aseries, wherein said movement element of a drive device is in each case connected or coupled to said base element of a following one of said drive devices.

13. The movement device according to claim 1, wherein said manipulator configuration has control systems for controlling and/or regulating said drive devices that said drive devices and said control systems are equipped for operation with increased and/or changing acceleration.

14. The movement device according to claim 1, wherein said functional head can be guided towards the body in a selectable position.

15. The movement device according to claim 1, wherein said functional head contains components selected from the group consisting of examination devices, treatment devices, an ultrasound measuring head, an optical recording device, an acoustic recording device, a resistance measuring device, an injection configuration, a liquid analysis configuration, a blood-taking device, an analysis device, a chemical analysis device, a radiation source outputting x-ray, gamma or infrared radiation, a laser source, a sample-taking device, a temperature measuring device, a current measuring device, a radiation detection device, an endoscopic examination device, a device for optical eye examination and/or further radiological, and invasive or contact devices for diagnostic or therapeutic purposes.

16. The movement device according to claim 1, wherein said manipulator configuration further comprising:
- at least one data input configuration; and
- a multi-axis control for controlling a movement of said functional head, said multi-axis control being provided such that a plurality of axes can be controlled simultaneously by said at least one data input configuration, and movement characteristics of the manipulator configuration can be adapted by transforming a control coordinate system to an arbitrary point, wherein a control point is place at a contact point of said functional head with the body.

17. The movement device according to claim 1, wherein said manipulator configuration further comprising:
- at least one control system; and
- at least one data input configuration, a movement of said functional head with respect to said base can be remote-controlled and/or automated by said at least control system and/or said at least one data input configuration.

18. The movement device according to claim 17, wherein said at least one data input configuration has input device selected from the group consisting of joysticks, slider controls, data globes, computer programs, and automated programs.

* * * * *